United States Patent [19]

Deffeves et al.

[11] Patent Number: 4,683,318

[45] Date of Patent: Jul. 28, 1987

[54] HYDROPHOBIC, CRYSTALLINE, MICROPOROUS SILACEOUS MATERIALS OF REGULAR GEOMETRY

[75] Inventors: Kenneth S. Deffeves, Princeton, N.J.; Aaron A. Rosenblatt, New York, N.Y.

[73] Assignee: The Scopas Technology Company, Inc., New York, N.Y.

[21] Appl. No.: 565,460

[22] Filed: Dec. 27, 1983

[51] Int. Cl.$^4$ ............................................... C07F 5/06
[52] U.S. Cl. ...................................................... 556/173
[58] Field of Search .......................................... 556/173

[56] References Cited

U.S. PATENT DOCUMENTS

| | | | |
|---|---|---|---|
| 2,911,386 | 11/1959 | Olson et al. | 260/46.5 |
| 3,488,368 | 1/1970 | Spivack | 260/429.7 |
| 3,507,897 | 4/1970 | Kanner et al. | 260/448.2 |
| 3,658,069 | 4/1972 | Wise | 131/10.7 |
| 3,682,996 | 8/1972 | Kerr | 260/448 C |
| 3,691,099 | 9/1972 | Young | 252/450 |
| 3,935,363 | 1/1976 | Burholder | 428/281 |
| 4,015,031 | 3/1977 | Reinhardt et al. | 427/213 |
| 4,151,189 | 4/1979 | Rubin et al. | 556/173 |
| 4,157,978 | 6/1979 | Llenado | 556/173 X |
| 4,346,021 | 8/1982 | Ball et al. | 556/173 X |
| 4,376,104 | 3/1983 | Ball et al. | 556/173 X |
| 4,434,103 | 2/1984 | Interrante | 556/173 |

FOREIGN PATENT DOCUMENTS

| | | | |
|---|---|---|---|
| 2305390 | 10/1976 | France | 427/213 |
| 2013476 | 8/1979 | United Kingdom | 556/173 UX |
| 2103196A | 2/1983 | United Kingdom | 556/173 |

OTHER PUBLICATIONS

Fenimore, et al., *Anal. Chem.*, vol. 48, p. 2284 (1976).
Barrer, et al., *Can J. Chem.*, vol. 42, p. 1481 (1964).
Chen, *J. Phys. Chem.*, vol. 80, p. 60 (1976).
Barrer, et al., *J.C.S. Faraday I*, vol. 74, p. 1871 (1978).
Harrison, et al., "Compendium of Organic Synthetic Methods", Wiley-Interscience, NV (1971), pp. 124–131.

*Primary Examiner*—Paul F. Shaver

[57] ABSTRACT

The present invention discloses a new family of crystalline, microporous silaceous materials of regular geometry which are substantially hydrophobic, and methods for their preparation. These compounds may be prepared from natural or synthetic hydrated aluminous tectosilicates.

19 Claims, 1 Drawing Figure

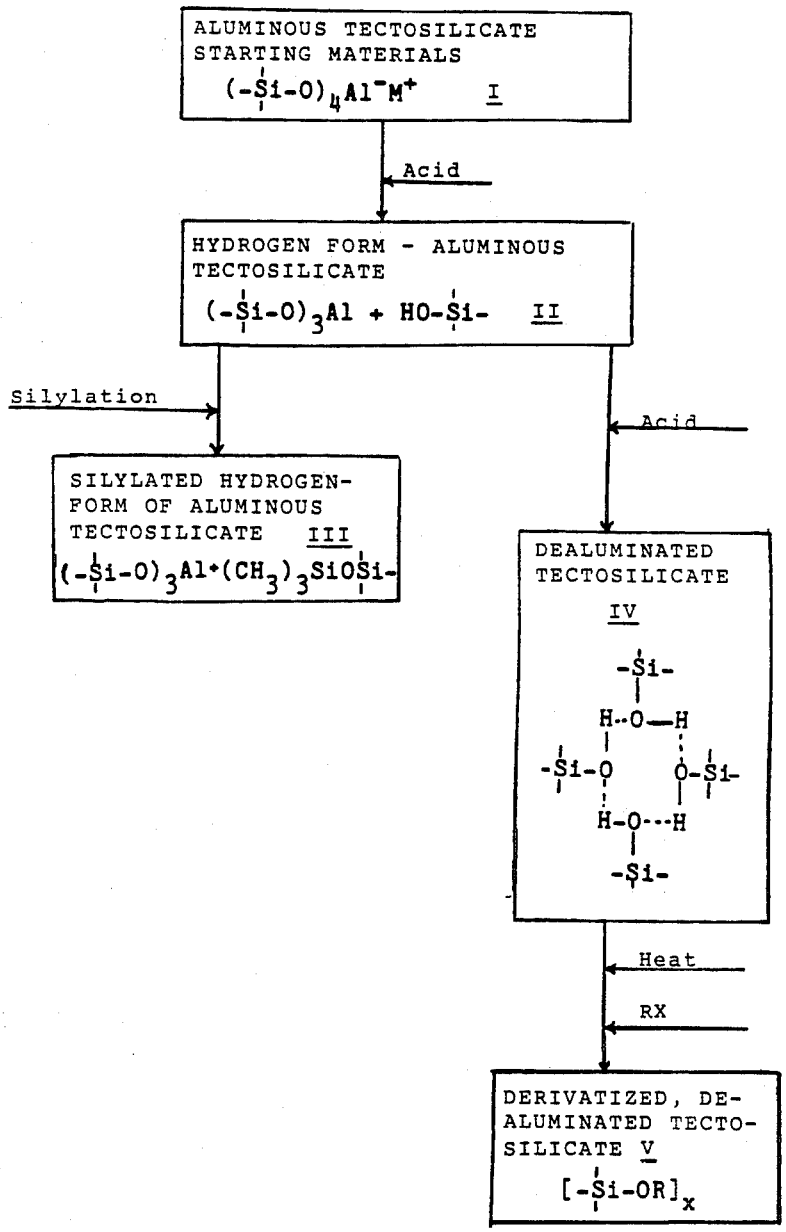
FIG 1. DERIVATIZATION OF TECTOSILICATES

HYDROPHOBIC, CRYSTALLINE, MICROPOROUS SILACEOUS MATERIALS OF REGULAR GEOMETRY

Crystalline, hydrated aluminous tectosilicates of Group I and Group II elements such as potassium, sodium, magnesium and calcium are formed in nature or may be synthesized in the laboratory, and higher polyvalent ions such as the rare earths are readily introduced by cation exchange. Structurally, these tectosilicates are aluminous "framework" silicates which are based on an infinitely extending three-dimensional network of $AlO_4$ and $SiO_4$ tetrahedra which link to each other by sharing oxygen ions. Such frameworks or lattices bear net negative charges and may be schematically represented by the general structural formula:

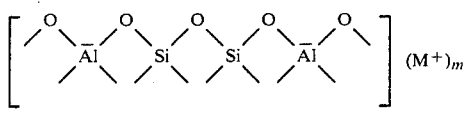

wherein $M^+$ is a cation such as sodium or potassium and m is equal to the number of negatively-charged aluminum ions within the lattice. The aluminous tectosilicates may also be represented by the empirical unit cell formula:

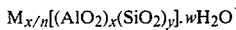

wherein M is the cation of valence n, w is the number of water molecules and the ratio y/x usually is about 1–10, depending on the structure of the particular tectosilicate involved. The sum (x+y) is the total number of tetrahedra in the unit cell; the portion within the brackets represents the framework composition of the tectosilicate.

After dehydration, some tectosilicates exhibit large internal surface areas which are available to absorb liquids or gases due to the clearing of the channels and pores, which channels uniformly penetrate the entire volume of the solid. The external surface of a tectosilicate represents only a small portion of its total available surface area. Therefore, a dehydrated tectosilicate will selectively sorb or reject different molecules on the basis of their effective molecular sizes and shapes. This size-selective sorption action may be total or partial. If total, the diffusion of one species into the solid may be wholly prevented while the diffusion of a second species occurs. If partial, the components of a binary mixture may diffuse into the solid at different rates, depending on the exposure conditions involved.

Due to the point electric charges on the surfaces of aluminous tectosilicate pores, highly polar molecules such as water, ammonia, alcohols and the like are generally more strongly sorbed than molecules of lower polarity such as hydrocarbons or inert gasses. Water is readily sorbed and tightly bound by aluminous tectosilicates. The water molecules have a strong tendency to cluster in fragments of a diamond-like lattice both in the liquid and in the vapor phase. This hydrophilicity has been exploited to remove water in either the liquid or vapor phase from mixtures of water and molecules such as the hydrocarbons processed by the petroleum industry. Gas streams comprising small readily-sorbed gas molecules such as nitrogen, hydrogen and the like may also be dried with dehydrated tectosilicates due to the tectosilicates' extremely strong attraction for water.

However, aluminous tectosilicate hydrophilicity has prevented the use of these materials to remove selectively less polar substances from mixtures containing water. For example, a tectosilicate which would remove significant quantities of dissolved ammonia from human excreta would find utility in a diaper or bed pad where it would act, at least in part, to prevent ammonia burn and thus to prevent ammonia dermatitis (diaper rash). Such materials would also be useful as a component in letter such as that used to sorb the excreta of farm animals or houshold pets. Although both naturally-occurring and synthetic tectosilicates have been used to remove nitrogenous components from liquid human and animal wastes through ion exchange, the problem of removing dissolved ammonia in the presence of large amounts of water has not been solved. See Burholder, U.S. Pat. No. 3,935,363. The preferential sorption of water molecules over the ammonia molecules quickly reduces the tectosilicates' ability to sorb ammonia.

The desirability of using tectosilicates as sorbents to remove carbon monoxide from tobacco smoke while permitting larger, flavor-imparting molecules to remain in the smoke has long been recognized. However, the realization of this goal has been effectively thwarted by the preferential sorption of water vapor which is also a component of tobacco smoke and which rapidly fills the tectosilicate pores, thereby preventing the sorption of significant amounts of carbon monoxide. One attempt to prevent this occlusion involves the use of a water-absorbing substance placed in the smoke stream upstream from the tectosilicate, as disclosed in U.S. Pat. No. 3,658,069. Metal catalysts have also been introduced into tectosilicates, for example, to oxidize carbon monoxide to carbon dioxide or to catalyze the hydrogenation and cracking of petroleum feedstocks. Such catalyst-supporting tectosilicates are also susceptible to deactivation by water through pore occlusion and catalyst poisoning, for example, see British Pat. No. 2,013,476A.

A tectosilicate material of hydrophobic character would overcome these poisoning and occlusion problems by being resistant to water sorption while otherwise maintaining affinity and activity for other molecular species. Such hydrophobic tectosilicates would be useful to remove inpurities from aqueous feedstocks as well as to protect introduced catalysts from deactivation by water.

Accordingly, it is an object of the present invention to provide a hydrophobic tectosilicate-based material which resists water sorption while retaining a useful affinity for other molecules.

It is another object of the present invention to provide a hydrophobic tectosilicate-based material that will strongly sorb ammonia while exhibiting a decreased hydrophilicity, preferably a hydrophilicity which is less than the material's power to absorb ammonia.

BRIEF DESCRIPTION OF THE INVENTION

The objects of the present invention have been attained by hydrophobic tectosilicates that are prepared by a reaction sequence that comprises removing a substantial part of the aluminum from the lattice sites of a naturally-occurring or synthetic aluminous tectosilicate so as to create reactive lattice sites, preferably hydroxyl-containing nests of general structure $(\equiv SiOH)_4$ in the silicaceous lattice of the tectosilicate. The resultant aluminum-deficient tectosilicates are dehydrated, e.g. by heating them, so as to drive off water of hydration without destroying or otherwise deactivating the reactive sites. The resultant materials are then derivatized so as to substitute selected moieties for the hydroxyl groups, said moieties being weaker point electric sources than aluminum or, preferably, than hydroxyl groups. Selection of the appropriate dealumination, dehydration and derivatization conditions in accord with the present invention results in the production of a new family of hydrophobic materials that are microporous, crystalline and that exhibit a stronger affinity for ammonia than for water under equivalent exposure conditions.

As used herein with respect to a substituent, the term "weaker point electric source" is defined as possessing a lower overall charge and/or which charge is distributed over a larger molecular volume than the charge distribution at, for example: (a) an aluminum site in an aluminous tectosilicate; (b) a hydroxyl site formed as a result of aluminum removal.

DETAILED DESCRIPTION OF THE INVENTION

The hydrophobic materials of the present invention are prepared by reacting lattice silyl hydroxyl groups, preferably those in the tetracoordinate "nest" configuration, so as to substitute organic moieties, preferably acyl, alkyl or silyl groups for the hydroxyl nests. Preferred silyl groups are those of the general formula $Si(R')_nX_p$ wherein n is 0–3, p is (3)-(n), R' is selected from the group consisting of aryl, alkyl, acyl, aralkyl, cycloalkyl and mixtures thereof and X is halogen or an alkoxy group. The preferred acyl, alkoxy and alkyl groups are lower acyl, alkoxy or alkyl radicals such as $C_1$–$C_4$ alkyl, alkoxy or acyl groups, both branched and straight chain. Preferably n is 1–2 and X is chloro.

The tectosilicates derivatized in this manner are first dealuminated so as to produce the requisite reactive sites in the silicaceous lattice, preferably by treatment with aqueous mineral acid. They are then dehydrated so as to expose these reactive sites. Although all tectosilicates may include some incidental structural hydroxyl (OH) groups, not enough hydroxyls are present to allow chemical derivatization to the extent necessary to impart useful degree of hydrophobicity. Accordingly, the substrate tectosilicates must first be treated to increase the number of lattice hydroxyl groups, and should then be dehydrated to make the hydroxyl groups available for subsequent chemical derivatization.

The general reaction scheme for the method of this invention may be depicted as outlined in FIG. 1. Replacement of the metal cation ($M^+$) of tectosilicates by hydronium ion is easily accomplished by exposure of tectosilicates to aqueous acid. As outlined in FIG. 1, a Si—O—Al bond of starting material I readily protonates and dissociates to provide aluminum-associated hydroxyl sites within the lattice as shown by structure II. Kerr (U.S. Pat. No. 3,682,996) has disclosed the silylation of these type II sites, i.e., by exposure to trimethylsilane ($HSi(CH_3)_3$) to form silylated, aluminum-containing materials of structure III. Kerr disclosed that type III silylated zeolites absorbed about 40% less cyclohexane, n-hexane and water than the parent "hydrogen" zeolites of type II. However, Kerr does not report any change in selectivity perference.

Aluminous tectosilicates having a silicon to aluminum ratio (Si:Al) of greater than about 5 can be almost totally dealuminated without loss of lattice integrity. See R. M. Barrer and M. B. Makki, *Can. J. Chem.*, 42, 1481 (1964). This has been accomplished by extended treatment of aluminous tectosiliates with aqueous acid. Dealumination is thought to afford tectosilicates having tetracoordinated hydroxylated nests comprising about 4 associated ≡Si—OH moieties, as depicted in structure IV. These aluminum-free sites may be termed "exoaluminum sites".

Activated tectosilicate materials both of structures II and IV would be expected to exhibit reduced hydrophilicity due to absolute reduction of lattice charge due to aluminum removal, but would still be expected to sorb water via hydrogen bonding to hydrogen atoms associated with the remaining aluminum atoms and/or to the free silyl hydroxyl (SiOH) groups. Heating aluminum-containing or dealuminated tectosilicates to relatively low temperatures, i.e., to about 100°–200° C., preferably in the presence of a vacuum, clears pores and channels for absorption by removing water of hydration from the pores. Exposure of dealuminated tectosilicates to higher temperatures, i.e., to about 400°–500° C., causes either partial or total destruction of the hydroxyl nests, via dehydroxylation and formation of new Si-O—Si bonds. N. Y. Chen in *J. Phys. Chem.*, 80, 60 (1976) has reported that dealuminized mordenites having Si:Al ratios of greater than 80 will not absorb water vapor at a pressure of one or 12 mm of mercury.

An early attempt to replace lattice aluminum with silicon by reaction of the nests with silane was unsuccessful. See R. M. Barrer and J.-C. Trombe, *J.C.S. Faraday I*, 74, 1871 (1978), who also reported the likelihood of some nest silylation to form a tectosilicate of structure V ($R=SiH_3$, $x<4$). They also reported that nest hydroxyl groups appeared to be less reactive to silylation than are the hydroxyl groups present in structure II of FIG. 1. The hydrophilicity of the silylated tectosilicates was not determined.

The aluminous tectosilicates utilized as starting materials in the present invention can include crystalline, amorphous and mixed crystalline amorphous tectosilicates of natural or synthetic origin or mixtures thereof. The water insoluble crystalline tectosilicates useful in the present invention are those that possess interstitial channels of a narrowest diameter of about 3–13 Å. Hereinafter this diameter will be referred to as pore size. A preferred pore size characterizing the underivatized substrate materials useful in this invention is about 3–10 Å, most preferably 4–8 Å. The pore size of any given tectosilicate must be larger enough to admit derivatization materials such as silanes, alcohols and the like, yet small enough to prohibit entry of unwanted liquid or gas stream components, i.e., aromatics, ketones, heterocyclic compounds and the like. Tectosilicates possessing pore sizes within the range of about 4–13 Å readily admit small gaseous elements and compounds such as water (kinetic diameter [$\sigma$]2.65 Å), carbon monoxide ($\sigma=3.76$ Å), carbon dioxide ($\sigma=3.30$ Å) and ammonia ($\sigma=2.60$ Å).

The most useful aluminous tectosilicate starting materials preferably will possess a lattice silicon to aluminum ratio of greater than about 5:1. Tectosilicates having a silicon to aluminum ratio of less than about five tend to lose their structural integrity upon dealumination.

An especially preferred class of aluminous tectosilicate starting materials is the naturally-occurring clinoptilolites. These minerals typically have the unit cell structure:

wherein the sodium ion content (Na+) may be partially replaced by calcium, potassium and/or magnesium, etc. The silicon:aluminum ratio in preferred varieties is greater than 5 and most preferably greater than about 8. The pore size is in the range of about 4.0–6.0 Å. Clinoptilolite is stable in air to about 700° C. and maintains its structural integrity upon dealumination.

Other naturally-occurring aluminous tectosilicates that are useful as starting materials are the mordenites, which typically exhibit the unit cell composition:

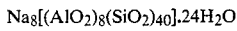

wherein calcium and potassium cations may replace a part of the sodium cations. The pore size is in the range of about 3.5–4.5 Å. The silicon to aluminum ratio is generally greater than 5.0 and may be greater than 10 in some samples. Other aluminous tectosilicates such as ferrierite or erionite would also provide useful starting materials.

Although naturally-occurring aluminous tectosilicates are the preferred starting materials due to their low cost and accessibility in large quantities, the synthetic analogs of the natural tectosilicates and their derivatives would be of equivalent utility in the present method. For example, synthetic mordenite (Zeolon ®), available from the Norton Company, would be an acceptable starting material for use in the present invention. Also, other synthetic, porous tectosilicates which have no equivalent in nature could serve as acceptable starting materials.

The formation of the hydrophobic materials of the present invention normally will proceed in three steps: (1) dealumination, (2) dehydration and (3) derivatization with an appropriate alkylating, acylating or silylating agent.

The dealumination of aluminous tectosilicates with acid is well known in the art. For example, R. M. Barrer and M. B. Makki in *Canadian J. Chem.*, 42, 1481 (1964) reported the complete dealumination of clinoptilolite by refluxing samples in aqueous hydrochloric acid of varying concentration. In the present method, a strong acid treatment is preferred, involving exposing pulverized, sieved aluminous tectosilicate to refluxing, i.e. boiling 2–10N aqueous mineral acid for about 1–3 hours. The preferred acid is about 3–7N hydrochloric acid, although other strong acids such as sulfuric acid, nitric acid or phosphoric acid may be useful in some cases.

In some cases, a mild acid treatment involving the percolation of aqueous acid through a column of crushed aluminous tectosilicate under ambient conditions has been found to be satisfactory. Prefrerably, the tectosilicate starting material will be dealuminated to a Si:Al ratio of greater than about 25, preferably the ratio will exceed 100, e.g. about 150–300, and under the most preferred conditions essentially no lattice aluminum will be retained, as measured by x-ray fluorescence.

The dealuminated, air-dried tectosilicate materials are then heated in order to remove most of the pore water of hydration and to expose the remaining lattice hydroxyl groups to derivatization. The heating can be carried out at any temperature sufficient to effect substantial dehydration without causing significant lattice rearrangement and subsequent loss of reactive sites. Typically the dealuminated materials are heated to about 100°–200° C. for about 10–40 hours, preferably under reduced pressure. Investigation of the effects of high temperatures, i.e., of 500°–600° C. on tectosilicates that had been subjected to the acid treatment at ambient temperatures indicated that, although substantial hydrophobicity was exhibited by the samples relative to the starting materials, the derivatization did not cause a further increase in hydrophobicity.

Following thermal dehydration at lower temperatures, e.g., about 100°–200° C., the dealuminated, dehydrated materials are allowed to cool and then are exposed to derivatizing reagents that react so as to functionalize the internal lattice silyl-hydroxyl groups, the majority of which are thought to be present in tetracoordinated nests of the unit structure IV, as depicted in FIG. 1. After exposure of the aluminum-free sites ("exoaluminum sites") to the derivatizing reagent, the nest sites will contain from about 1–4 [Si—OR] units wherein R is alkyl, acyl, or silyl substituted with 1–3 halogen, alkoxy alkyl, aryl, aralkyl or cycloalkyl substituents wherein the alkyl, alkoxy or acyl groups, either directly attached to the lattice silyloxy or bound to the silicon atom of the R group, preferably are $C_1$–$C_4$ alkyl, alkoxy or acyl groups.

Reagents (RX) useful to replace the hydrogen atom of the nest silyl-hydroxyl groups with the substituent R include a wide range of the reagents known in organic chemistry to be useful to alkylate, acylate or silylate hydroxyl groups. Such agents are generally disclosed by I.T. Harrison et al. in *Compendium of Organic Synthetic Methods,* Wiley-Interscience, N.Y. (1971) at pages 124–131, the disclosure of which is incorporated by reference herein. Preferred reagents include the lower-$C_1$–$C_4$-alkanols or $C_1$–$C_4$ alkyl halides such as methanol, ethanol and the like or methyl chloride, methyl iodide, ethyl chloride, butyl bromide and the like. Lower-$C_1$–$C_4$-alkanols have been found to be especially effective as derivatizing agents when thermally reacted with the tectosilicates under pressure either neat or in the presence of catalysts. Other useful alkylating reagents include the $C_1$–$C_4$-diazo-alkanes.

Nest hydroxyl groups may be acylated by exposure to ketenes such as ketene itself or to alkyl or dialkyl ketenes such as dimethylketene. Reaction of a silylhydroxyl group with ketene affords an SiOR moiety wherein R is acetyl, while reaction with dimethylketene introduces R as dimethylacetyl.

A wide variety of silylation reagents may be used to introduce substituted silyl substituents into the tectosilicate nests, i.e., to introduce R as $[Si(R')_nX_p]$ wherein n is 0–3, p is (3)−(n), R' is selected from the group consisting of $C_1$–$C_4$ lower alkyl, $C_5$–$C_7$ cycloalkyl, aryl, $C_1$–$C_4$-acyl, aralkyl and mixtures thereof; and X is a halogen atom, i.e., Cl, F, I, Br or mixtures thereof, or a (lower) alkoxy group.

Di-, tri- or tetrafunctional silylation reagents may also react with 2–4 ≡Si—OH groups in a single nest to functionally replace the missing aluminum atom with the bridging unit $SiR'_q$, wherein q is 0–2, thus bridging the aluminum-deficient site with 1–2 silicon atoms. This reaction would occur via the elimination of 2–4 HX groups and the formation of O—Si—O bridges. For example, when dimethyldichlorosilane is reacted with lattice silyl hydroxyl groups (≡Si—OH), structural units such as ≡SiOSi(CH$_3$)$_2$Cl or ≡SiOSi(CH$_3$)$_2$OSi may be introduced into the nests. Of course, themethyl groups may be replaced with any of the groups represented by R' and Cl may be replaced by another halogen atom or by an alkoxy group.

Typical monofunctional silylating reagents which introduce Si(R')$_3$ units include trimethylchlorosilane, trimethylfluorosilane, dimethyliso-propyl-chloro-silane and the like. Preferred difunctional silylating agents include the dihalodialkylsilanes, e.g., dichlorodimethylsilane and the dialkoxy(dialkyl)silanes, e.g, diethoxydimethylsilane. Tri- and tetrafunctional silanes may also be employed to derivatize the tectosilicates of the present invention, such as silicon tetrafluoride, tetrachlorosilane, and trifluoromethylsilane.

Reaction of the dealuminated, dehydrated tectosilicates with the silylation reagent may be carried out by contacting the materials with the reagent in the liquid or gas phase. Preferably, an excess of silylation reagent in a suitable solvent is slurried with the tectosilicate. Heating and/or added catalysts may be employed if necessary, depending on the reactivity of the tectosilicate and the silane.

Gaseous hexamethyldisilazane can be reacted with lattice hydroxyl groups to introduce trimethylsilyl groups into the nests, following the procedure of Fenimore et al., *Anal. Chem.*, 48, 2289 (1976), the disclosure of which is incorporated herein by reference.

The methods of the present invention readily afford hydrophobic microporous, crystalline silaceous materials which exhibit a greatly reduced affinity for water while maintaining high affinities for less polar molecules such as ammonia. The hydrophobicity or reduction in hydrophilicity of a tectosilicate can be quantitated in terms of its absorption of water per unit of tectosilicate under a given set of exposure conditions (retention volume). That any observed reduction in water retention is due to hydrophobicity as opposed to a general reduction in retention can be established by measuring the retention of a similarly-sized molecule of comparable or lesser polarity, such as ammonia, nitrogen, methane or carbon dioxide. By the use of these general techniques, the derivatization methods of the present invention provide microporous crystalline silaceous materials that exhibit an affinity for water vapor as measured in terms of retention (ml of $H_2O$/g of material at STP), which is reduced an additional 10-50%, preferably about 15-45% under the absorption capacity observed prior to the derivatization step but after the tectosilicates have been acid treated and activated toward derivatization by heating. When ammonia vapor retention is used as a reference, the absorption of water vapor into the derivatized material is no more than about 20-80% that of ammonia and is probably much less. In contrast, both ammonia and water are irreversibly absorbed on heat dehydrated or hydrated tectosilicate samples which have not been treated with acid or derivatized, exhibiting retention volumes of greater than 200 ml of vapor per column-gram of aluminous tectosilicate under the gassolid chromatography conditions used to measure the retention volumes.

The invention will be further illustrated by reference to the following examples.

The following six procedures were used to modify the properties of clinoptilolite (Hector, Cal., NL Industries).

PROCEDURE A$_1$ - MILD ACID WASH

The tectosilicate, i.e., clinoptilolite, was crushed in a jaw crusher, then pulverized in a Braun Pulverizer. The pulverized material was passed through a 50-100 mesh RoTap ® sieve agitator and used to fill a 2-inch diameter, 3-foot long Pyrex ® tube two-thirds full. The powdered material was held in place with a glass wool plug. Forty liters of hydrochloric acid (6N) were flowed through the packed column at a rate of about 9 ml/min. at 27° C. The acid-treated material was washed by flushing with three column volumes of distilled water, then air-dried. Clinoptilolite (Hector, Cal.) treated in this manner was light green and exhibits a Si:Al ratio of approximately 30.

PROCEDURE A$_2$ - STRONG ACID WASH

The light green material (225 g) isolated from procedure A$_1$ was placed in a 4.0 liter round bottomed flask and 2.0 l of 6N HCl was added. The slurry was heated at reflux for 2.0 hours. A white mineral was recovered by vacuum filtration and washed repeatedly with deionized water. The Si:Al ratio of clinoptilolite treated in this manner was about 212.

PROCEDURE H$_1$ - MILD HEAT TREATMENT

About 10 g of pulverized tectosilicate (clinoptilolite) was placed in a 250 ml beaker and heated to 150° C. for 20 hours in a vacuum drying oven at less than 10 mm Hg. After vacuum heating, the material was stored at 150° C. at ambient pressure.

PROCEDURE H$_2$ - HIGH HEAT TREATMENT

About 10 g of pulverized tectosilicate (clinoptilolite) was placed in a quartz 250 ml beaker and heated at 550° C. for 14 hours at ambient pressure, then transferred to a 150° C. oven for storage at ambient pressure.

PROCEDURE D$_1$ - SILYLATION

Pyridine was allowed to stand over potassium hydroxide pellets for 24 hours, then distilled from barium oxide and stored over 4 Å molecular sieves. Toluene was refluxed over sodium metal for three days, then distilled and stored over Linde type 4A molecular sieves. A reagent mixture of 20% pyridine, 15% dichlorodimethylsilane and 65% toluene was prepared and stored over the molecular sieves.

A 250 ml round bottomed flask equipped with magnetic stirring, a reflux condenser and an argon inlet was flushed with dry argon and charged with 10 g of pulverized tectosilicate followed by addition of 100 ml of the reagent mixture described hereinabove. The resultant slurry was refluxed for 20 hours. After reaction, the acid-treated tectosilicate material was isolated by filtration and washed with dry toluene and methanol. The material was refluxed for at least two hours in methanol, recovered by filtration and stored under ambient conditions.

PROCEDURE D$_2$ - METHYLATION

About 5.0 g of pulverized material was placed in a steel bomb with about 50 ml of methanol. The bomb was sealed and heated to 220° C. for 4-12 hours. The bomb was cooled to 25° C. and the material recovered by filtration.

DETERMINATION OF GAS RETENTION VOLUMES

The treated, pulverized tectosilicate was vacuum-packed into a silylated glass column (0.125 inch inner diameter, 0.25 inch outer diameter) and held in by plugs of silylated glass wool. The column was inserted into the oven of a gas chromatograph. The injector port was maintained at 200° C., the detector oven at 250° C. and the column maintained at an initial conditioning temperature of 45°-50° C. for 10-30 minutes. The detector filament current was held at 150 mA and the carrier gas (He) inlet pressure was 60 psi. Gas injections (75-125 $\mu$l) were made at 4-7 psi above ambient pressure and liquid injections were of 1-2 $\mu$l. Water and ammonia retention volumes were measured at a column temperature of 200° C. Under these conditions, ammonia was irreversibly absorbed. Results were expressed as K (ml of gas absorbed/g of absorbent at STP).

The properties of a number of modified Hector, California clinoptilolites prepared by various combinations of the procedures described above are summarized in Table I. In all cases the procedures were performed or omitted in the order indicated. The silicon: aluminum ratios were determined by energy-dispersive x-ray spectrometry (Tracor Spectrace model 440, Tracor-Northern 2000 Analyzer) with data reduction accomplished using the program Super ML, Tracor X-Ray, Inc.

TABLE I

| Ex. | Treatment | $K(H_2O)^1$ | Si/Al | Total Carbon Analysis (%)[4] |
|---|---|---|---|---|
| 1 | none | >200 | 10.00 | 0.28 |
| 2 | $A_2H_1D_2$ | 21 | High[2] | 0.69 |
| 3 | $A_2H_1D_1$ | 27 | High[2] | 0.62 |
| 4 | $A_2H_1D_0$ | 36 | 211.67 | 0.12 |
| 5 | $A_1H_1D_2$ | 58 | 39.58 | 0.52 |
| 6 | $A_1H_2D_0$ | 59 | 6.93[3] | 0.30 |
| 7 | $A_1H_2D_1$ | 64 | 32.66 | 0.63 |
| 8 | $A_1H_1D_1$ | 79 | 33.00 | 2.37 |
| 9 | $A_1H_1D_0$ | 93 | 34.43 | 0.38 |
| 10 | $A_1H_0D_2$ | 129 | 33.56 | 0.29 |
| 11 | $A_1H_0D_0$ | >200 | 10.82[3] | N.T. |
| 12 | $A_1H_0D_1$ | >250 | 39.01 | 2.90 |
| 13 | $A_1H_2D_2$ | >570 | 6.8[3] | 0.36 |

[1] ml/g at STP; $K(NH_3)$ was >200 in all cases.
[2] Lattice Al not detected in these materials.
[3] Anomalous results probably due to operator error.
[4] Galbraith Laboratories, Inc., Knoxville, Tenn.

From the results tabulated on Table I it can be generally seen that combinations of mild or strong acid washes followed by high or low temperature heating significantly increases the hydrophobicity of the tectosilicate even without a further derivatization step. The effect is most pronounced in the case of samples washed with strong acid, then heated at 150° C. ($A_2H_1D_0$ Ex. 4). However, examples 3 and 2 demonstrate that a further significant increase in hydrophobicity can be attained by silylation or methylation, respectively, or this material. The total percent carbon is also increased in these samples by over 400% in each case. Likewise, an increase in hydrophobicity is observed in the case of the silylation (Ex. 8) or methylation (Ex. 5) of the material of Ex. 9, which had been subjected to the mild acid wash and then to 150° C. heating. The greater affinity for water observed for these materials as opposed to the materials of examples 3 and 2 is thought to reflect the presence of more reactive sites, i.e., silyl nests, in the latter two materials, which had been exposed to stronger dealumination conditions.

However, Examples 7 and 13 indicate that no increase in hydrophobicity was observed for the material of Ex. 6 when derivatization was attempted; rather, a decrease was observed. It is thought that the failure of derivatization to affect the observed hydrophobicity in the case of the material of Ex. 6 is due to the collapse of hydroxyl nests or other reactive sites formed by the initial acid wash. Furthermore, a comparison of Example pairs 8 and 7, 9 and 6 indicates that, for otherwise equivalently-prepared samples, a high heat treatment ($H_2$) results in a significantly lower carbon incorporation when either methylation or silylation is attempted. This provides further support for a mechanism involving the production and preservation of activated nests following the strong acid, mild heat treatment combination. The attempted silylation (Ex. 12) of material which had been acid washed but not dehydrated (by heat) failed to increase the hydrophobicity of the material of Ex. 11, possibly due to the blockage of reactive sites by water of hydration. Methylation of the same material caused a moderate increase in hydrophobicity (Ex. 10).

The hydrophobic derivatized materials of Exs. 3 and 2 also possessed no detectable lattice aluminum by x-ray fluoroscopy, a negative result also expected and observed in the case of Silicalite ® (Union Carbide). This provides confirmation that the strong acid wash conditions are effective to remove lattice aluminum and produce reactive hydroxyl-containing nests that are available for derivatization. Although removal of lattice aluminum is, by itself, adequate to significantly increase the hydrophobicity of the clinoptilolite, and, in fact, is the major contributor to the hydrophobic properties involved, it is apparent from Examples 8, 3, 5 and 2 that the hydrophobic properties are optimized, for this set of treatment variables, by further silylation or methylation. Significant hydrophobic affects are generally observed in both derivatized and underivatized materials when the Si:Al ratio exceeds about 25.

The hydrophobic materials prepared according to examples 8, 3, 5 and 2 would be expected to absorb significant amounts of ammonia from wet human or animal excreta, and to do so more effectively than any material employed heretofore, such as underivatized tectosilicates, phyllosilicate clays, silica gel and the like. To this end, the new materials may be incorporated in diapers, bedpads and the like, either in vapor- or moisture- permeable compartments or distributed throughout the textile matrix. For example, in the case of a bedpad or disposable diaper which typically consists of an absorbent core of natural or synthetic fibers, a permeable top or inner sheet and a liquid-impervious back or outer sheet, an effective amount of the new material of the instant invention can be incorporated in the absorbent core of the disposable diaper. The amount of ammonia-absorbent used can vary from about 1% to 50%, preferably about 15% to 25% (based on the weight of the diaper), depending on whether the diaper is intended for day or night use; and on the age of the user. Additionally, an effective amount of the new material may be solution-coated onto a disposable diaper top sheet, incorporated into the absorbent lining of plastic baby pants or incorporated into cloth diapers by known methods in the art of dispersing particulate solids into fibrous substrates.

The new hydrophobic materials of this invention may also be employed as animal litter, preferably when aggregated into pellets, either alone or in combination with other absorbent materials. Typical animal litter consists of absorbent inorganic or organic materials such as attapulgite, vermiculite and calcium montmorillonite (i.e., clay), agglomerated wood dust, wood chips, dehydrated grasses, straw, or alfalfa, fly ash and the like. The addition of an effective amount, e.g. about 5-95%, preferably about 20% to 30% or more (based on total litter weight) of the new material to these litters will enhance the deodorizing capabilities of the litter without substantially reducing the litter absorbent characteristics.

The new hydrophobic materials of this invention may also be used in filter cartridges in pipes, cigars or cigarettes, either alone or dispersed throughout and/or deposited on conventional tobacco smoke filtration materials. Used in this capacity, effective amounts of the new hydrophobic materials would be expected to absorb significant amounts of carbon monoxide from the mainstream smoke more effectively than hydrophilic materials commonly used in smoke filters such as cellulose, activated carbon, naturally-occurring or synthetic aluminous tectosilicates and the like. For example, a filter can be made having a section consisting of about 10–75 mg, preferably about 40 to 50 mg of the new hydrophobic material either front of or behind the standard filter material. Additionally, about 10–40 mg, preferably about 20 to 30 mg of the new material may be incorporated in the standard filter material itself. Likewise, effective amounts of the powdered materials of this invention could be incorporated into wrapping materials such as paper and tobacco leaf used to shape cigarettes or cigars in order to reduce the carbon monoxide in the sidestream smoke of the burning cigar or cigarette. The amount used will depend upon the total weight, volume and composition of the wrapping material used.

While certain representative embodiments of the invention have been described herein for purposes of illustration, it will be apparent to those skilled in the art that modifications therein may be made without departing from the spirit and scope of the invention.

We claim:

1. A hydrophobic microporous crystalline tectosilicate material of regular geometry comprising aluminum-free sites in a silaceous lattice that are characterized by the presence of about 1–4 associated moieties of the formula $\equiv$SiOR wherein R is a substituent that is a weaker point electric source than aluminum.

2. The material of claim 1 wherein R is a substituent that is a weaker point electric source than a hydroxyl group.

3. The material of claim 2 wherein R is a substituent selected from the group consisting of $C_1$-$C_4$ alkyl, $C_1$-$C_4$ acyl, and $SiR'_n X_p$ wherein R' is selected from the group consisting of $C_1$-$C_4$-alkyl, cycloalkyl, aryl, $C_1$-$C_4$acyl, aralkyl and mixtures thereof, X is a halogen atom or a (lower)-alkoxy group, n is 0–3 and p is (3)–(n).

4. The material of claim 2 wherein the aluminum-free site is bridged by 1–2 of the units $SiR'_q$ wherein q is 0–2, and wherein R' is selected from the group consisting of $C_1$-$C_4$-alkyl, cyloalkyl, aryl, $C_1$-$C_4$ acyl, aralkyl and mixtures thereof.

5. The material of claim 3 or 4 wherein said sites are created by a process comprising removing aluminum from an aluminous tectosilicate lattice.

6. The material of claim 5 wherein R is $C_1$-$C_4$ lower alkyl or $SiR'_n Cl$ wherein R' is $C_1$-$C_4$ alkyl and n is 1–2.

7. The material of claim 5 wherein the lattice Si:Al ratio after aluminum removal is greater than about 25.

8. The material of claim 7 wherein the lattice is essentially aluminum-free.

9. The material of claim 1 which exhibits an absorption of water vapor which is no more than about 20–80% the absorption of ammonia vapor.

10. A method for preparing a hydrophobic microporous crystalline material of regular geometry comprising:
    (a) creating aluminum-deficient sites in the lattice of a natural or synthetic aluminous tectosilicate starting material, said sites being characterized by the presence of about 4 associated $\equiv$SiOH moieties;
    (b) heating the aluminum-deficient tectosilicate to remove water of hydration;
    (c) reacting the $\equiv$SiOH moieties with a derivatizing reagent whereby about 1–4 of said moieties per site are converted to a moiety of the formula $\equiv$SiOR wherein R is a substituent which is a weaker point electric source than aluminum.

11. The method of claim 10 wherein R is a substituent selected from the group consisting of $C_1$-$C_4$ alkyl, $C_1$-$C_4$ acyl and $SiR'_n X_p$ wherein R' is selected from the group consisting of cycloalkyl, aryl. acyl alkyl, aralkyl and mixtures thereof, X is halo or (lower)alkoxy, n is 0–2 and p is (3)–(n), or whereby 2–4 of the Si-OH moieties are bridged by the unit $SiR'_q$ wherein q is 0–2.

12. The method of claim 11 wherein reaction of two of the $\equiv$Si—OH moieties with the derivatizing agent results in the elimination of two HX molecules and the bridging of the moieties by the unit —$SiR_2$—.

13. The method of claim 11 wherein R is $C_1$-$C_4$ alkyl or R' is $C_1$-$C_4$ alkyl, n is 1-2 and X is chloro.

14. The method of claim 10 wherein the Si:Al ratio of the starting material is greater than about 5:1.

15. The method of claim 11 wherein the aluminum deficient sites are created by exposure of the aluminous tectosilicate to aqueous mineral acid.

16. The method of claim 15 comprising removing essentially all of the aluminum from the aluminous tectosilicate lattice.

17. A method for decreasing the hydrophilicity of a tectosilicate material comprising:
    (a) removing a substantial portion of the aluminum from the lattice sites of an aluminous tectosilicate to create aluminum deficient sites characterized by about 4 associated $\equiv$SiOH moieties;
    (b) dehydrating the aluminum-deficient tectosilicate at a temperature at which the integrity of the lattice is retained: and
    (c) reacting the $\equiv$SiOH moieties with a derivatizing reagent selected from the group consisting of dihalodialkylsilanes, dialkoxydialkylsilanes, $C_1$-$C_4$-alkanols and $C_1$-$C_4$ alkylhalides whereby about 1–4 of said moieties per site are converted to a moiety of the formula:

$$\equiv SiOR$$

wherein R is selected from the group consisting of $C_1$-$C_4$ alkyl or $SiR_2 X$ wherein X is a halogen atom; or whereby at least two $\equiv$SiOH moieties per site are bridged by the unit $SiR'_q$ wherein q is 0–2.

18. The method of claim 17 wherein the derivatizing agent is dichlorodimethylsilane or methanol.

19. The method of claim 17 wherein the starting material is a clinoptilolite.

* * * * *